United States Patent [19]

Orbán et al.

[11] Patent Number: 5,047,396

[45] Date of Patent: Sep. 10, 1991

[54] INTRAVENOUS PHARMACEUTICAL COMPOSITION AND PROCESS FOR PREPARING THE SAME

[75] Inventors: Erno Orbán; Tibor Balogh; Lajos Ila; Gábor Ambrus; Antónia Jekkel; Sándor Elek; Éva Tomori; István Elekes; Éva T. Sarudy; Imre Moravcsik, all of Budapest; Lajos Siklósi, Gödöllo, all of Hungary

[73] Assignee: Biogal Gyogyszergyar, Debrecen, Hungary

[21] Appl. No.: 383,024

[22] Filed: Jul. 21, 1989

[30] Foreign Application Priority Data

Jul. 21, 1988 [HU] Hungary .............................. 3796/88

[51] Int. Cl.$^5$ ...................... A61K 37/02; C07K 7/64
[52] U.S. Cl. .......................................... 514/11; 514/9; 514/885; 514/922; 514/943; 514/970; 530/317; 530/321
[58] Field of Search ..................... 530/317, 321; 514/9, 514/11, 885, 922, 970, 943

[56] References Cited

U.S. PATENT DOCUMENTS 4,388,307  6/1989  Cavanak ................................. 514/11

Primary Examiner—Lester L. Lee
Assistant Examiner—Christina Chan
Attorney, Agent, or Firm—Keil & Weinkauf

[57] ABSTRACT

The present invention relates to an intravenous pharmaceutical composition comprising cyclosporin as active ingredient. The composition is composed of
  a) 1 part by mass of one or more cyclosporins,
  b) 8 to 13 parts by mass of a monoester of a saturated hydroxylated fatty acid formed with polyethylene glycol or the mixture of said monoesters,
  c) 4 to 10 parts by mass of one or more intravenously administerable mono- or polivalent alcohols.

The invention further relates to a process for preparing such composition.

7 Claims, 2 Drawing Sheets

—— C+S   3 mg/kg i.v.
—·—· C+C

INTRAVENOUS PHARMACEUTICAL COMPOSITION AND PROCESS FOR PREPARING THE SAME

The present invention relates to an intravenous pharmaceutical composition comprising cyclosporin as active ingredient. Furthermore the invention relates to a process for preparing this composition.

Cyclosporins are cyclic oligopeptides produced by microorganisms. Cyclosporin A, C and G exhibit significant immunosuppressive effect. Cyclosporin A is widely used when organs (kidney, heart, lungs, liver, pancreas) are transplanted in order to inhibit the rejection provoked by the transplanted organ and when bone marrow is transplanted cyclosporin A is given to prevent graft-versus-host disease. Cyclosporin A is also successfully used for the treatment of Autoimmune disorders (e.g. diabetes juvenilis, rheumatoid arthritis, uveitis, psoriasis).

Cyclosporins are formed from neutral amino acids of hydrophobic character and are insoluble in water. Their poor solubility in water causes that they are not absorbed or only partly absorbed in the organism when administered together with usual pharmaceutical excipients, therefore these compositions are not suitable for therapeutical use.

Cyclosporins have to be dissolved or dispersed in a colloid system if they are aimed to be used in therapeutical practice.

In order to make cyclosporins usable in therapy, the following solutions were worked out:

1. So-called "solid solutions" are prepared by using polyethylene glycols of high molar mass (Chion, W. L., Riegelman, S.: J. Pharm. Sci. 60, 1281 /1971/).

2. Cyclosporin is dissolved in natural oils and the solution thus obtained is encapsulated (van Hoff, J. P. et al.: 1987, II. 1456).

3. Cyclosporin is dissolved in the mixture of a trans esterification product of a natural vegetable oil triglyceride, a polyalkylene glycol, ethanol and a vegetable oil (Austrian patent specification No. 375,828, U.S. Pat. No. 4,388,307).

4/ Cyclosporin is dissolved in a mixture of ethanol and CREMOPHOR EL (polyoxyethylated castor oil, produced by BASF, Ludwigshafen, Germany) (Sandimmun Product Information, Chapter XII, Sandoz-Pharma, Basle, 1984).

The products prepared according to method 1 are not suitable for parenteral use, they are pellet particles which can be administered orally.

The products prepared according to method 2 are also suitable for oral administration only.

The products prepared according to method 3 are not suitable for intravenous administration due to their oil content, therefore they can be used subcutaneously or intramuscularly.

The intravenous administration of compositions prepared according to method 4 is well known in the art. However, they suffer from the drawback that they are not well-tolerable by the patients, i.e. after administration they often cause anaphylactic reactions which are dangerous from the point of view of the patient (Kahan et al.: Lancet, 1984, I:52; Leunissen, K. M. L. et al.: Lancet, 1985, I:636; Howrie, D. L. et al.: Drug Intell. Clin. Pharm. 19 425 /1985/).

The anaphylactic reaction does not occur when cyclosporin is administered in different compositions, therefore it has been stated that the polyoxyethylated castor oil is exclusively responsible for causing the anaphylactic reaction (CREMOHPOR EL, Technical Leaflet MEF 074e, BASF, Ludwigshafen, 1984). Though the activity of CREMOPHOR was thoroughly studied, there is no literary reference teaching the moiety of the molecule which is responsible for the dangerous side-effect.

Therefore our aim was to work out an intravenous pharmaceutical composition comprising cyclosporin as active ingredient which is more tolerable than the known intravenous formulations, i.e. its anaphylactic-hypersenzibilizing effect is smaller than that of the known formulation.

Now we have found that if cyclosporin is dissolved in the mixture of an alcohol suitable for intravenous administration and a monoester of a saturated hydroxylated fatty acid formed with polyethylene glycol, the occurrence and extent of the toxic side-effects can be significantly be decreased or fully eliminated.

As the monoesters of saturated hydroxylated fatty acids formed with polyethylene glycol are structurally similar to CREMOPHOR, it could not be expected by a man skilled in the art that the occurrence of the toxic side-effects can be overcome by using these compounds.

The intravenous pharmaceutical composition containing cyclosporin as active ingredient of the present invention comprises a) 1 part by mass of one or more cyclosporins,
b) 8 to 13 parts by mass of a monoester of a saturated hydroxylated fatty acid formed with polyethylene glycol on the mixture of such monoesters,
c) 4 to 10 parts by mass of one or more intravenously administerable mono- or polyvalent alcohols.

The composition according to the invention is prepared by mixing a) 1 part by mass of one or more cyclosporins,
b) 8 to 13 parts by mass of a monoester of a saturated hydroxylated fatty acid formed with polyethylene glycol or the mixture of such monoesters,
c) 4 to 10 parts by mass of one or more intravenously administerable mono- or polyvalent alcohols.

The pharmaceutical compositions according to the invention are suitable for the intravenous administration of the hydrophobic cyclosporin A, G, C or the mixture thereof which are insoluble or poorly soluble in the usual pharmaceutical excipients and enable the administration of the said cyclosporins in an aqueous solution. The cyclosporins can be used in any mass ratio related to each other in the composition of the invention.

As components b) of the pharmaceutical composition according to the invention, the monoesters of $C_{10-22}$ preferably $C_{14-22}$, more preferably $C_{16-20}$ saturated hydroxylated fatty acids formed with polyethylene glycol (PEG) of a molar weight of 600 to 1300, preferably 750 to 1100 or the mixture of such monoesters of any mass ratio can be used. Especially preferred monoesters are PEG-9-hydroxymiristate, PEG-9-hydroxypalmitate and PEG-12-hydroxystearate wherein the PEG moiety has a molar weight of 750 to 1150, or the mixtures thereof in any mass ratio.

These compounds can be prepared e.g. by the method of Chandrasekhara Rao, T. et al. (J. Am. Oil Chem. Soc., 54, 18, /1977/). Polyethylene glycol-12-hydroxystearate is commercially available. These components b) can dissolve the hydrophobic cyclosporins in the presence of co-solvents even at room temperature.

As co-solvent component c) mono- or polyvalent alcohols, suitable for intravenous administration, or the mixture of such alcohols in any mass ratio can be used. Examples for such alcohols include e.g. ethyl alcohol, propylene glycol, polyethylene glycol or the mixture thereof.

The pharmaceutical composition according to the invention can be prepared by mixing the cyclosporin with component c), then dissolving component b) in the solution thus obtained. According to an other embodiment, component b) can be mixed to component c), and the active ingredient can be dissolved in the solution thus obtained. The mixing is preferably carried out at 10° to 50° C.

The compositions thus prepared can be formulated with or without further pharmaceutical excipients suitable for parenteral use, but they have to be diluted to the desired active ingredient content before use in therapy as the pharmaceutical compositions thus prepared are concentrates which cannot directly be used for intravenous administration.

As parenterally administerable, suitable excipients distilled water or aqueous solutions, e.g. infusion solutions such as saline, glucose, dextrane, fructose, mannitol solutions can be mentioned. The dilution depends on the desired active ingredient content of the injection, thus the compositions of the invention are generally diluted in a mass ratio of 1:20 to 1:100 with water or a suitable solution.

The amount of cyclosporin to be administered in the pharmaceutical composition according to the invention will naturally depend upon the disease to be treated, the age and condition of the patient, the seriousness of the illness, etc.

The therapeutically effective amount of cyclosporins is well known. When using compositions of the present invention a daily dose of from about 3 mg/kg to about 50 mg/kg is ssuggested in order to treat chronic inflammations or to provoke an immunosuppressive effect.

The solution composed of the above components can be directly filled into ampoules or it can be supplemented with appropriate amount of distilled water and the aqueous solution can be filled into ampoules.

Before filling into ampoules, the solutions have to be filtered to germ-free. This can be made by using e.g. a regenerated cellulose membrane of a pore size of 0.2 $\mu$m. The filling of the solution into ampoules is generally carried out in the presence of air or an inert gas, e.g. nitrogen and then the ampoules are closed.

The compositions according to the invention are stable over long periods of time at lower temperatures, e.g. at 5° C., such as are commonly employed for storage of pharmaceuticals in hospitals and at elevated temperatures, e.g. at 75° C. Therefore the compositions have a good shelflife, their active ingredient content does not precipitate even after long storage and they also have reduced temperature criticality.

The pharmaceutical composition according to the invention comprises known and easily available excipients and it can easily be prepared. Simultaneously, the drawback of the known compositions comprising cyclosporin as active ingredient is substantially eliminated when the composition of the present invention is used in therapeutical practice.

The invention is further illustrated by the following, non-limiting examples.

EXAMPLE 1

Parenteral Composition Comprising Cyclosporin A as Active Ingredient 65 g of SOLUTOL HS 15 (chemical name: polyethylene glycol-660-12-hydroxystearate, produced by BASF, Ludwigshafen, Germany) is mixed to 30 ml of 96% ethanol (USP XXI quality), then 5 g of cyclosporin A are dissolved at room temperature in the mixture thus obtained.

The solution thus obtained is made up to 100 ml with 96% ethanol (USP XXI quality). The liquid is homogenized by stirring and filtered germ-free through a cellulose membrane filter of a pore size of 0.2 $\mu$m of SARTORIUS SM 11607 type. The filtered solution is filled into ampoules under nitrogen atmosphere, and the ampoules filled with 5.3 ml of solution are closed. The composition thus obtained can be used for intravenous administration after dilution with e.g. isotonic saline solution, glucose, dextrane, fructose or mannitol solution.

Example 2

Parenteral Composition Comprising Cyclosporin A as Active Ingredient 35 g of polyethylene glycol-800-9-hydroxy miristate and 30 g of polyethylene glycol-850-9-hydroxy palmitate are mixed to 20 ml of 1,2-propanediol (of USP XXI quality), then 5 g of cyclosporin A are dissolved under stirring in the mixture thus obtained while the temperature of the mixture is kept at 50° C.

The solution thus obtained is supplemented to 100 ml with distilled water suitable for injection. The liquid is filtered to germ-free as described in Example 1 and filled into ampoules (5.3 ml of liquid in each ampoule) under argon atmosphere.

The composition can be used for intravenous administration after dilution as described in Example 1.

Example 3

Parenteral Composition Comprising Cyclosporin C as Active Ingredient 55 g of polyethylene glycol-850-9-hydroxypalmitate are mixed to 20 ml of polyethylene glycol 300 (of USP XXI quality), then 5 g of cyclosporin C are dissolved in the mixture thus obtained while the solution is heated to a temperature of 50° C.

Further on the solution is handled as described in Example 2.

The composition can be used for intravenous administration after dilution according to Example 1.

Example 4

Parenteral Composition Comprising Cyclosporin G as Active Ingredient 5 g of cyclosporin G are dissolved in 20 ml of 96% ethanol (USP XXI quality) and mixed with 65 g of polyethylene glycol-950-12-hydroxy stearate, preferably SOLUTOL HS 15. The solution thus obtained is made up to 100 ml with 96% ethanol (USP XXI quality). The liquid is homogenized by stirring and filtered to germ-free as described in Example 1, and filled into ampoules (5.3 ml of liquid in each ampoule) under nitrogen atmosphere.

The composition can be used for intravenous administration after dilution as described in Example 1.

EXAMPLE 5

Parenteral Composition Comprising Cyclosporin A as Active Ingredient 60 g of polyethylene glycol-950-12-hydroxystearate, preferably solutol HS 15 (BASF, Germany) are dissolved in 10 ml of 96% ethanol (of USP XXI quality), then 5 g of cyclosporin A are dissolved in the mixture thus obtained.

Further on the process according to Example 1 is followed.

The composition can be used for intravenous administration after dilution as described in Example 1.

STABILITY TEST

The stability of the compositions according to Examples 1 to 5 was examined. 10 ampoules each comprising the solutions prepared according to Examples 1 to 5 were stored at a temperature of 0° C., 5° C., 25° C., 60° C. and 75° C. and the change in the composition of the formulation was tested by high pressure liquid chromatography.

After 9 months standing no precipitation could be observed in any of the samples. Upon examining the content of the ampoules by HPLC, no trace of decomposition of any component could be found.

The potential anaphylactic-hypersenzibilizing effect and vein damaging effect of composition according to Example 1 (C+S) and the commercially available SANDIMMUN® (Sandoz) (C+C) (cyclosporin+CREMOPHOR+ethanol) were compared in order to demonstrate the more preferable effect of the composition according to the present invention over the known composition.

1. TESTING OF HYPERSENZIBILIZING EFFECT

The method of W. Lorenz and A. Schmal (Agents and Actions 12, 1/2 (1982)) suitable for determining the anaphylactic effect of solubilizing agents was followed.

The tests were carried out on Beagle dogs narcotized by NEMBUTAL®. The animals had spontaneous breathing. Two polyethylene canules were led into the vessels of the dogs: one into the abdominal aorta via the right femoral artery in order to measure the systemic (systolic and diastolic) blood pressure, the other into the caval vein inferior in order to administer the composition into the body and for taking blood samples to determine the histamine level. Parallelly with the measurement of the blood pressure, the heart rate and the breathing frequency were also measured. The occurence of other clinical symptoms (erythema, oedema, cutaneous allergic reactions) appearing due to the administering of the compositions was also studied. After a 20 minute equilibric time following the operation, the basic values were determined and the tests were repeated 2, 5, 10 and 20 minutes after the administration of the compositions (i.v. bolus injection, without dilution). The compositions were administered in a dose of 3 and 10 mg/kg body weight.

The effect of the compositions to the blood pressure and heart rate was evaluated by variancy analysis. The oedema and skin colouring reactions were classified into four categories. The effect of the compositons to the systolic and diastolic blood pressure (FIGS. 1 and 4), to the heart rate (FIGS. 2 and 5) and to the breathing frequency (FIGS. 3 and 6) and to the skin symptoms (Table I) are summarized in FIGS. 1 to 6 and Table I.

On the basis of the results of the test it can be established that the composition according to the present invention (C+S) administered at low dose (3 mg/kg body weight) does not have any significant cardiovascular effect (does not cause significant hypotension and bradycardia), while the comparative composition (C+C) significantly decreases the blood pressure and heart rate even at this lower dose.

When the compositions are administered at higher dose (10 mg/kg body weight), the composition according to the present invention (C+S) has essentially more moderate cardiovascular effect than the comparative composition (C+C).

There is no significant difference between the breathing frequency increasing effect of the compositions examined.

When the compositions were administered in a dose of 3 mg/kg, both compositions caused oedema and erythema, however, when the composition of the present invention (C+S) was administered in a dose of 10 mg/kg, the skin reactions practically disappeared. Thus—considering the hypersenzibilizing effect—the composition according to the present invention is more preferable than the comparative, known composition (C+C).

2 TESTING OF LOCAL VEIN DAMAGING EFFECT

The local vein damaging effect was tested on newzealandian rabbits. The two compositions were diluted to 20-folds volume with physiological saline solution, and 0.2 ml were injected into the vein of one ear, while physiological saline solution was injected into the vein of the other ear.

In the third and fourth group of test animals the solubilizing agents SOLUTOL and CREMOPHOR and carriers (ethanol) were tested. The compositions comprising SOLUTOL plus ethanol and CREMOPHOR plus ethanol were diluted to 20-folds volume with physiological saline solution and they were administered in the same dose (0.2 ml) into the vein of the ear of the test animals, while only physiological saline solution was injected into the vein of the other ear.

The local reactions were observed 24, 48 and 72 hours after the treatment. At this latter time the animals were deblooded and the tissues were examined.

The composition of the present invention (C+S) was as well tolerated as the comparative composition (C+C).

As a summary, it can be stated that the composition of the present invention causes lower hypersenzibilizing effect than the comparative composition. The difference is significant especially in respect of blood pressure decreasing effect. As to the local tolerancy, the composition of the present invention is equivalent with the comparative composition, while regarding the systemic tolerancy (hypersenzibilizing effect), it is more preferable.

Figure 1:
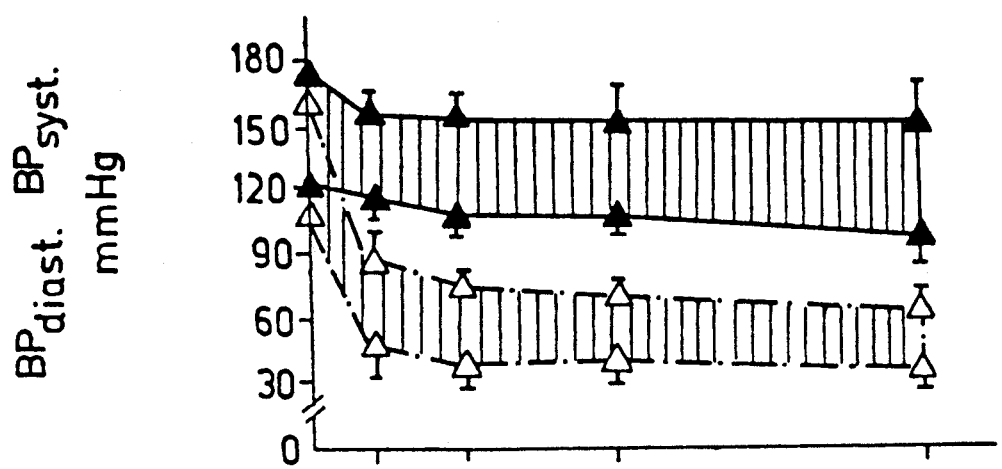
FIGS. 1-6 are graphs which demonstrate the effect of C+S and C+C on blood pressure, heart rate, and breathing rate.
Figure 2:
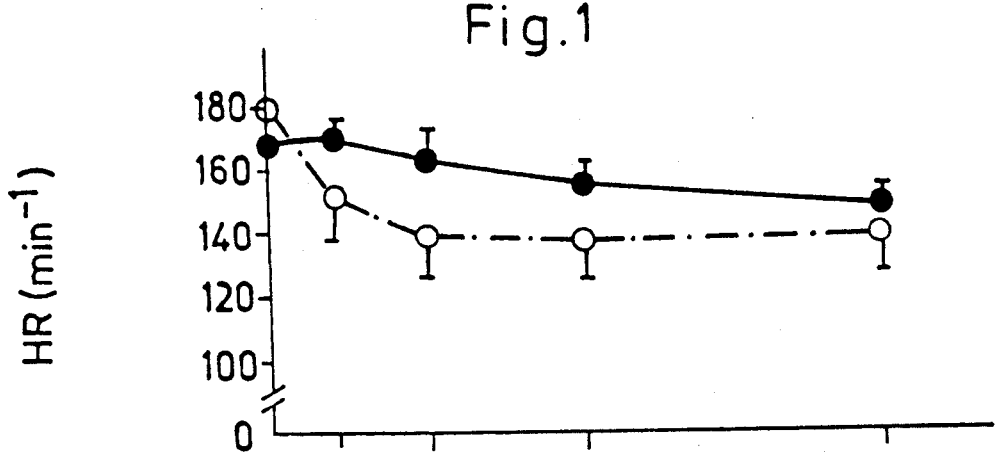
Figure 3:
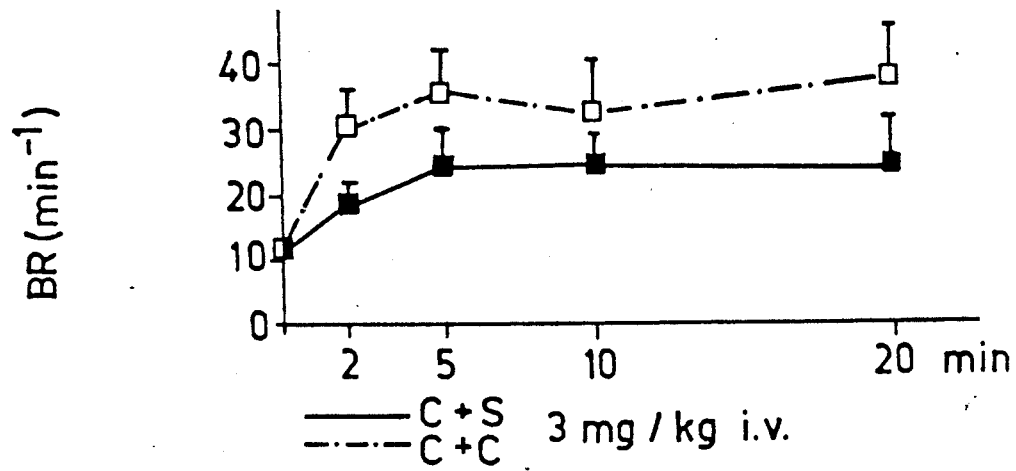
Figure 4:
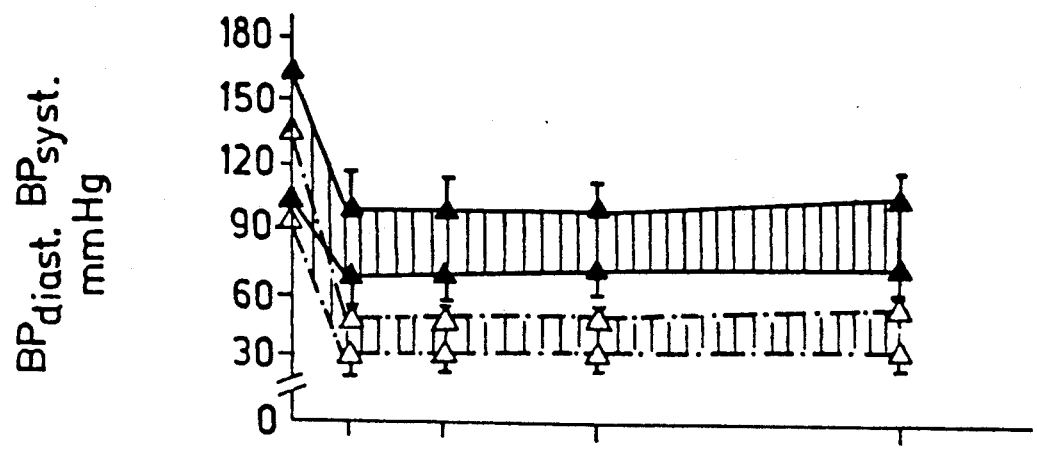
Figure 5:
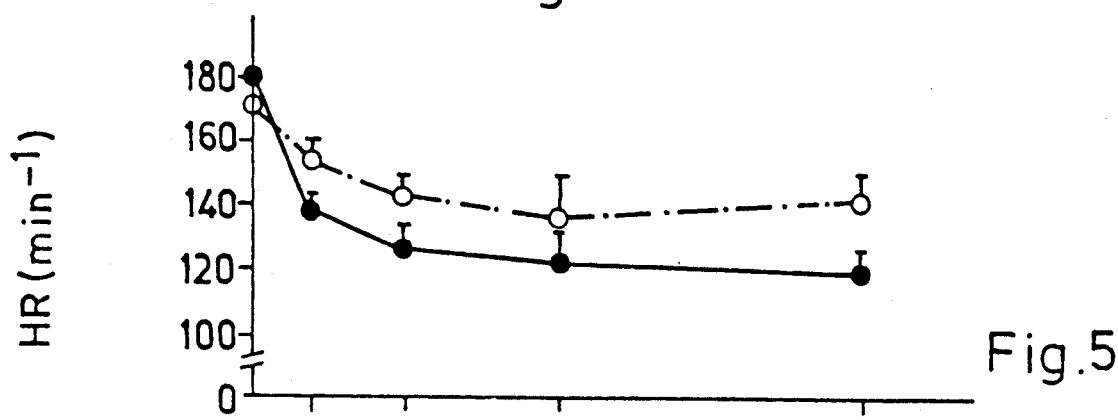
Figure 6:
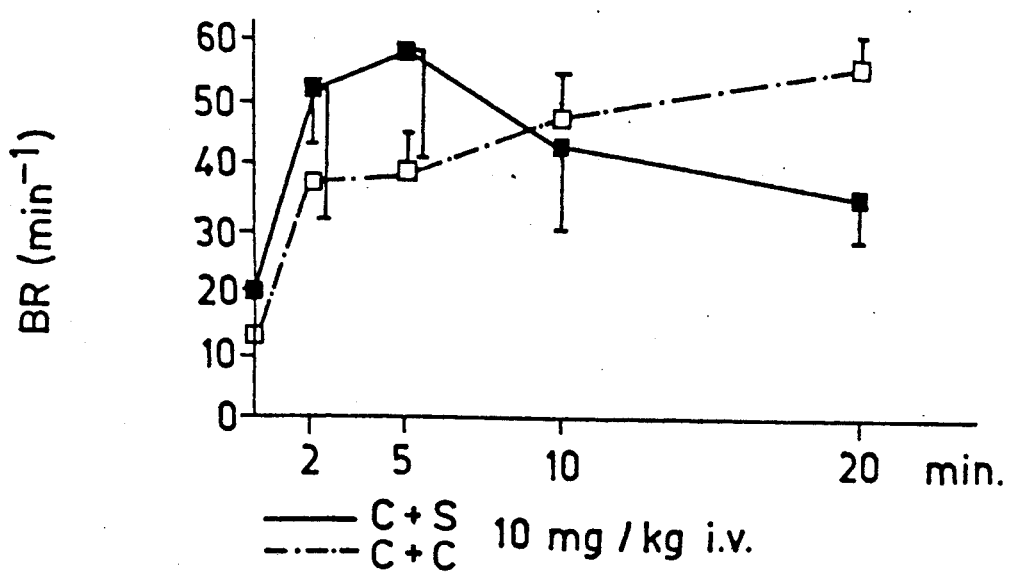

In the drawings, "diast." refers to diastolic, "syst." refers to systolic, "C+S" refers to cyclosporin plus SOLUTOL and "C+C" refers to cyclosporin plus CREMOPHOR.

TABLE I

The effect of compositions C + S (cyclosporin + solufol) and C + C (cyclosporin + cremophor) (3 mg/kg body weight, i.v.) to the erythemic symptoms

| Composition | No. of beagle dog | Measure of oedema | Measure of erythema |
|---|---|---|---|
| C + S | I. | 3 | 3 |
| 3 mg/kg | IV. | 1 | 1 |
| i.v. | IX. | 1 | 1 |
| n = 6 | XV. | 1 | 1 |
|  | XVI. | 1 | 1 |
|  | XVII. | 0 | 0 |
| C + C | II. | 1 | 2 |
| 3 mg/kg | III. | 1 | 1 |
| i.v. | XIV. | 1 | 1 |
| n = 5 | XVIII. | 1 | 1 |
|  | XIX. | 1 | 1 |
| C + S | XXV. | 0 | 0 |
| 10 mg/kg | XXVI. | 0 | 0 |
| i.v. | XXVII. | 1 | 0 |
| n = 5 | XXVIII. | 0 | 0 |
|  | XXIX. | 0 | 0 |
| C + C | XX. | 1 | 1 |
| 10 mg/kg | XXI. | 1 | 1 |
| i.v. | XXII. | 2 | 1 |
| n = 5 | XXIII. | 1 | 2 |
|  | XXIV. | 0 | 1 |

Meaning of marks:
0 - no effect
1 - weak effect
2 - medium effect
3 - strong effect

We claim:

1. Intravenous pharmaceutical composition comprising cyclosporin as active ingredient which comprises
   a) 1 part by mass of one or more cyclosporins,
   b) 8 to 13 parts by mass of a monoester of a saturated hydroxylated fatty acid formed with polyethylene glycol or the mixture of said monoesters,
   c) 4 to 10 parts by mass of one or more intravenously administerable mono- or polyvalent alcohols.

2. The composition according to claim 1 which comprises one or more members of the group consisting of cyclosporin A, cyclosporin C and cyclosporin G as cyclosporin.

3. The composition according to claim 1 which comprises one or more members selected from the group of monoesters of $C_{10-22}$ saturated hydroxylated fatty acids formed with polyethylene glycol (PEG) of a molecular weight of 600 to 1300 as component b).

4. The composition according to claim 1 which comprises one or more members of the group consisting of monoesters of $C_{14-22}$ saturated hydroxylated fatty acids formed with polyethylene glycol (PEG) of a molecular weight of 750 to 1100 as component b).

5. The composition according to claim 1 which comprises one or more members of the group consisting of polyethylene glycol-9-hydroxymyristate, polyethylene glycol-9-hydroxypalmitate and polyethylene glycol-12-hydroxystearate as component b).

6. The composition according to claim 1 which comprises polyethylene glycol-660-12-hydroxystearate as component b).

7. The composition according to claim 1 which comprises one or more members of the group consisting of ethyl alcohol, propylene glycol and polyethylene glycol as component c).

* * * * *